United States Patent

Campin et al.

(10) Patent No.: US 9,456,739 B2
(45) Date of Patent: Oct. 4, 2016

(54) METHOD FOR ASSESSING RESIDUAL ACCOMMODATION IN PRESBYOPIC EYES

(71) Applicant: NOVARTIS AG, Basel (CH)

(72) Inventors: John A. Campin, Southlake, TX (US);
George H. Pettit, Fort Worth, TX (US);
Daniel W. Stanley, Midlothian, TX (US)

(73) Assignee: NOVARTIS AG, Basel (CH)

(*) Notice: Subject to any disclaimer, the term of this patent is extended or adjusted under 35 U.S.C. 154(b) by 175 days.

(21) Appl. No.: 14/532,858

(22) Filed: Nov. 4, 2014

(65) Prior Publication Data

US 2015/0173600 A1    Jun. 25, 2015

Related U.S. Application Data

(60) Provisional application No. 61/918,877, filed on Dec. 20, 2013.

(51) Int. Cl.
| | | |
|---|---|---|
| *A61B 3/14* | (2006.01) | |
| *A61B 3/00* | (2006.01) | |
| *A61B 3/117* | (2006.01) | |
| *A61B 3/10* | (2006.01) | |

(52) U.S. Cl.
CPC ............. *A61B 3/0025* (2013.01); *A61B 3/10* (2013.01); *A61B 3/102* (2013.01); *A61B 3/1173* (2013.01)

(58) Field of Classification Search
CPC ... A61B 3/0025; A61B 3/102; A61B 3/1173
USPC ................................... 351/206, 209, 210
See application file for complete search history.

(56) References Cited

U.S. PATENT DOCUMENTS

| | | |
|---|---|---|
| 5,843,188 A | 12/1998 | McDonald |
| 2005/0041210 A1 | 2/2005 | Isogai et al. |
| 2008/0177170 A1 | 7/2008 | Roberts et al. |
| 2009/0096987 A1* | 4/2009 | Lai .................. A61B 3/113 351/206 |
| 2011/0160852 A1 | 6/2011 | Mentak et al. |
| 2012/0038883 A1 | 2/2012 | Peyman et al. |
| 2012/0053459 A1 | 3/2012 | Eilers et al. |

OTHER PUBLICATIONS

PCT/US2014/063929, "International Search Report", International Searching Authority, Feb. 17, 2015, 2pgs.
PCT/US2014/063929, "Written Opinion", International Searching Authority, Feb. 17, 2015, 3 pgs.

* cited by examiner

*Primary Examiner* — Huy K Mai
(74) *Attorney, Agent, or Firm* — Jason Finch

(57) ABSTRACT

A system for determining an accommodative force in a patient includes a sensor adapted to detect motion of a lens of the patient relative to a globe of the patient's eye, a controller configured to determine an accommodative force in the patient based on the relative motion and to determine at least one parameter for an intraocular lens based on the accommodative force, and an interface adapted to output the at least one parameter for the intraocular lens.

14 Claims, 2 Drawing Sheets

METHOD FOR ASSESSING RESIDUAL ACCOMMODATION IN PRESBYOPIC EYES

This application claims the priority of U.S. Provisional Application No. 61/918877 filed Dec. 20, 2013.

TECHNICAL FIELD

This invention relates generally to the field of accommodating intraocular lenses and, more particularly, to a method for assessing residual accommodation in presbyopic eyes.

BACKGROUND OF THE INVENTION

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and ultrasonically vibrated. The vibrating cutting tip liquefies or emulsifies the lens so that the lens may be aspirated out of the eye. The diseased lens, once removed, is replaced by an IOL.

In the natural lens, distance and near vision is provided by a mechanism known as accommodation. The natural lens is contained within the capsular bag and is soft early in life. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can focus alternatively on near and far objects.

As the lens ages, it becomes harder and is less able to change its shape in reaction to the tightening of the ciliary muscle. Furthermore, the ciliary muscle loses flexibility and range of motion. This makes it harder for the lens to focus on near objects, a medical condition known as presbyopia. Presbyopia affects nearly all adults upon reaching the age of 45 to 50. Various accommodative intraocular lenses (IOLs) have been proposed. However, it can be difficult to assess the accommodative response in particular eyes, making it likewise difficult to predict how an implanted IOL will respond.

SUMMARY OF THE INVENTION

Various embodiments of the present invention provide sensors for assessing residual accommodative function. In a particular embodiment, a system for determining an accommodative force in a patient includes a sensor adapted to detect motion of a lens of the patient relative to a globe of the patient's eye, a controller configured to determine an accommodative force in the patient based on the relative motion and to determine at least one parameter for an intraocular lens based on the accommodative force, and an interface adapted to output the at least one parameter for the intraocular lens. The embodiments discussed below are exemplary, and various changes can be made to these illustrative embodiments without deviating from the scope of the invention. For example, the features of one embodiment can be combined with those of another embodiment.

DETAILED DESCRIPTION

Figure 1:
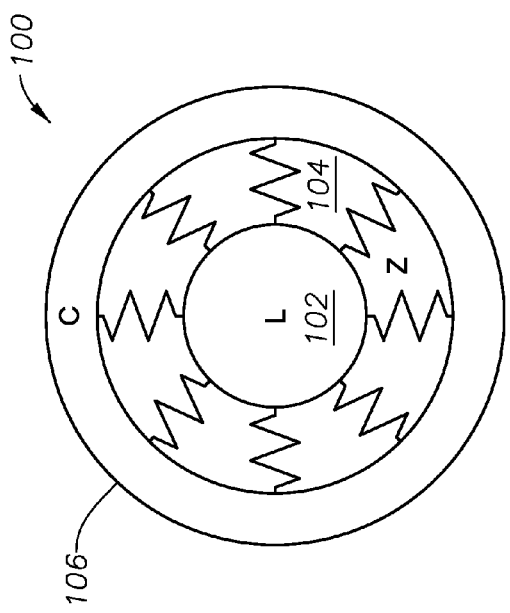
FIG. 1 is a schematic depicting a mechanical model of a patient's eye.

As shown in FIG. 1, the eye 100 can be illustrated mechanically as a system in which the lens 102 is suspended by zonules 104 attached to the ciliary body 106, causing the lens to be flattened by the tension in the zonules. As a patient accommodates, the ciliary body 106 contracts, and the tension in the zonules 104 is reduced, allowing the lens 102 to become more round. The change in tension when the zonules are tightened or slackened reflects the residual accommodative force in a presbyopic eye.

The lens 102 floats in liquid (vitreous and aqueous humor) within the eye 100. This allows the lens 102 to move relative to the surrounding eye tissue forming the globe of the eye, including the sclera and cornea. Ordinarily, the zonule tension is such that the lens 102 moves simultaneously with the eye 100, such as when the head turns. However, rapid eye movements can cause the lens 102 to lag behind the movement of the eye 100. This is the case with saccadic motions, rapid movements of the eye corresponding to changes between points of fixations. During a saccade, the eye 100 moves rapidly enough that the lens 102 can lag behind. This causes a wobble in the lens 102 as the tension in the zonules causes the lens 102 to settle back into position.

One technique for measuring residual accommodative force is to compare the wobble caused by saccadic motion when the patient is accommodating versus when the patient is not accommodating. The lens 102 can be modeled as a damped harmonic oscillator with a spring constant k representing the elastic tension in the zonules and a damping force reflecting the surrounding viscous fluids. The time required for the oscillations to stop then can be used to model the corresponding zonular tension.

Figure 2:
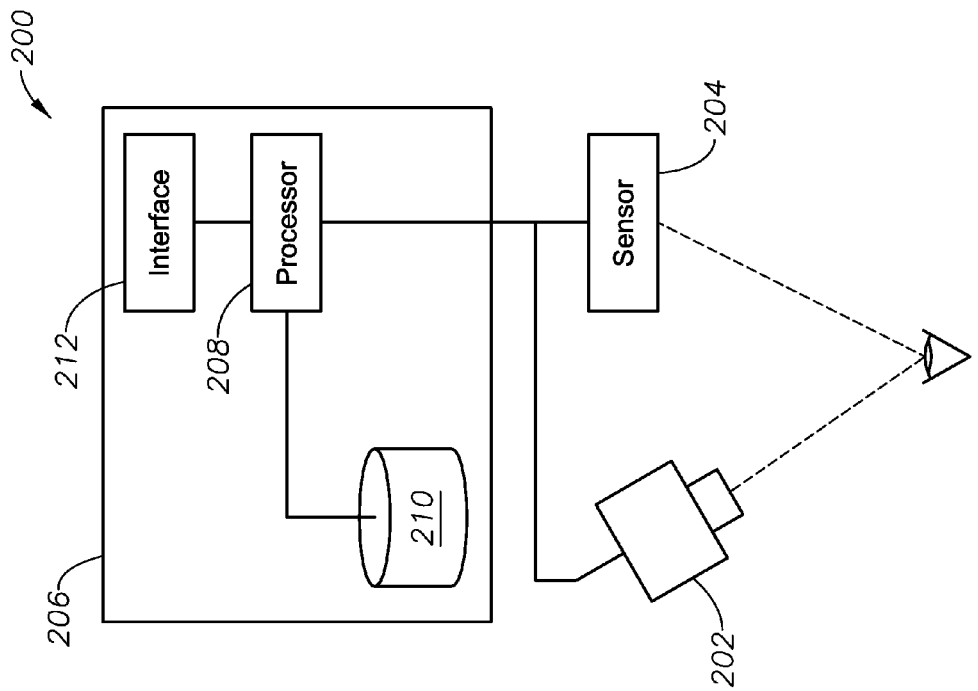
FIG. 2 is an example system for determining an accommodative force in a patient.

FIG. 2 illustrates an example system 200 for measuring the oscillations of the lens 102 relative to the eye. The system 200 includes a light source 202, a photosensor 204 and controller 206. The controller 206 include a processor 208, a memory 210 and a user interface 212. In the example embodiment, the light source 202 projects light onto a patient's eye. The light source 202 can also generate a suitable fixation pattern within the patient's field of view to cause the patient to accommodate or disaccommodate as needed. The photosensor 204 measures the reflections of light from the patient's eye in order to provide an indication of the relative location of the lens 102 relative to the globe of the eye 100. In an example embodiment, the photosensor 204 can record Purkinje reflections from various interfaces in the eye, such as the first and fourth Purkinje reflections corresponding to the anterior corneal surface and the posterior lens surface, respectively. The Purkinje reflections can likewise be used to track the relative motion of the lens 102 and the globe of the eye 100 using known techniques for eye tracking, thus providing an indication of the degree of oscillation.

The controller 206 includes the processor 208, which may include any microprocessor, microcontroller, integrated circuit, or other suitable electronic components suitable for processing electronic information. The memory 210 may be any volatile or non-volatile information storage suitable for storing information for processor 208, including magnetic, electronic, or optical storage. The interface 212 allows the system 200 to exchange information with a user of the system, including input devices such as a keyboard, keypad, touch screen or mouse controller and output devices such as a monitor or a printer.

In operation, the controller 206 receives signals from the photosensor 204 indicative of the relative motion of the lens 102 and the globe of the eye 100 during saccadic motion, determines the relative zonular tension in accommodating and disaccommodating states, and calculates the residual accommodative force in the patient's eye based on the comparison. As noted previously, this comparison can be based on a damped harmonic oscillator model that accounts for the viscosity of the surrounding fluid with the zonules applying a different spring force when tightened and slackened. The system 200 can then output the calculated accommodative demand via the interface 212. The output can be a direct measurement of the residual accommodative force, or it can instead represent a selection of an intraocular lens for the patient that responds to the accommodative demand.

In the case of intraocular lens selection, there could be a selection from a variety of lens models or an adjustment of an adjustable lens parameter to provide the needed combination of accommodation with the residual accommodation of the patient. In one example, a variety of accommodative lenses could be designed with varying haptic shapes or other mechanical features that provide a different response depending on the accommodative force exerted on the lens. In another example, there may be a tension adjustment or distance adjustment in the haptics of the lens that can be set based on the measurement of the residual accommodation force. In another example, an accommodative lens might be a liquid-filled, curvature changing lens that changes accommodative power as force is exerted on it, and the amount of liquid used to fill the lens could be adjusted to alter the mechanical response. In short, any suitable parameter that varies as a function of accommodative force could conceivably be selected or adjusted based on the residual accommodation measured.

Other alternative systems for measuring the relative motion of the lens and the globe of the eye could include ultrasound or optical coherence tomography (OCT) techniques. In general, any suitable method for locating the relative positions of the lens to the globe of the eye with sufficient resolution and acquisition speed could in principle be adapted for the present invention. Therefore, while a light source and photosensor as disclosed as an example above, any sensor for measuring the position of the lens relative to the globe can function within the system 200.

Figure 3:
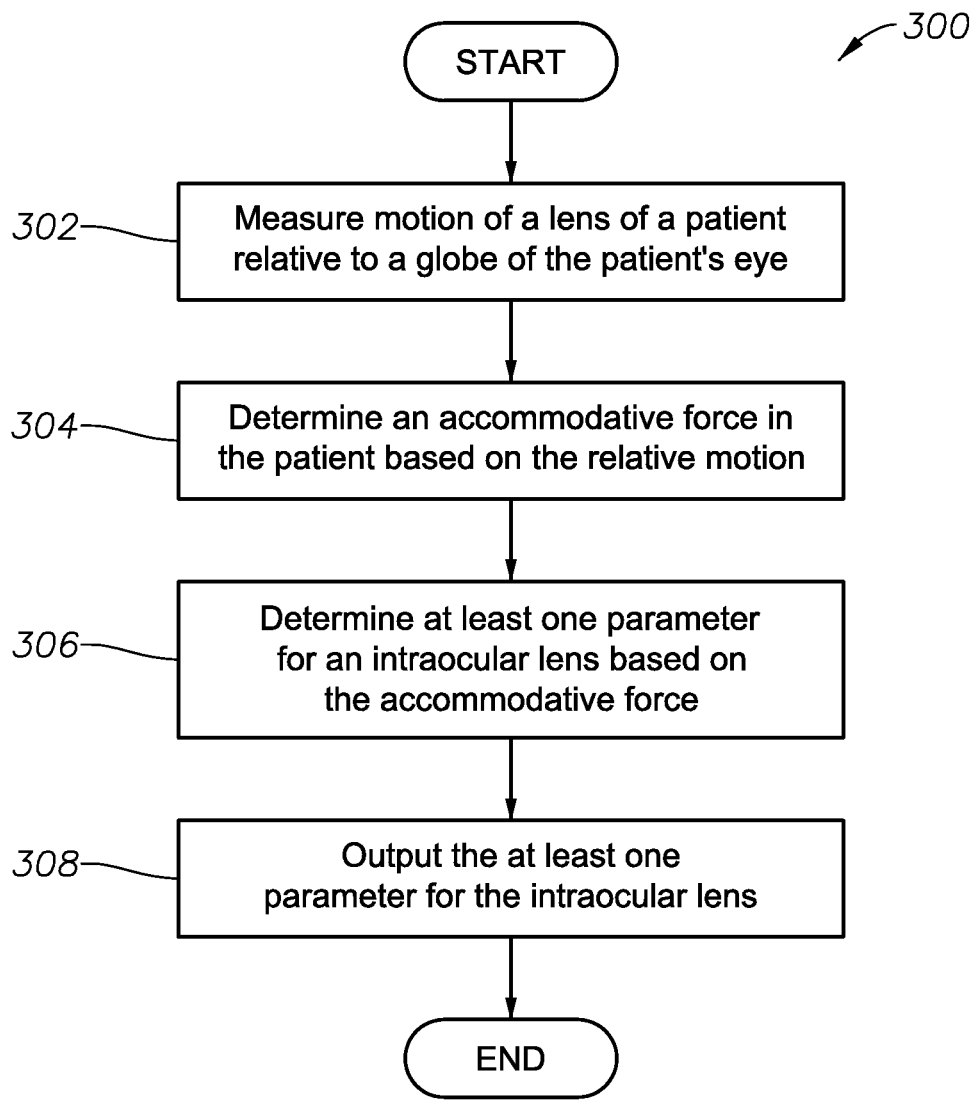
FIG. 3 is an example method for determining at least one intraocular lens parameter based on a determination of accommodative force in a patient.

FIG. 3 is a flowchart 300 of an example method of determining a parameter for an intraocular lens according to a particular embodiment of the present invention. At step 302, the method includes measuring motion of a lens of a patient relative to a globe of the patient's eye. The method then includes determining an accommodative force in the patient based on the relative motion at step 304. Next, at step 306, the method includes determining at least one parameter for an intraocular lens based on the accommodative force. Finally, at step 308, the method includes outputting the at least one parameter for the intraocular lens. The various method steps can be performed using any suitable apparatus according to any embodiment of the invention described herein or other suitable variations apparent to one skilled in the art.

Those having ordinary skill in the art will appreciate that various changes can be made to the above embodiments without departing from the scope of the invention.

What is claimed is:

1. A system for determining an accommodative force in a patient, comprising:
   a sensor adapted to detect motion of a lens of the patient relative to a globe of the patient's eye;
   a controller configured to determine an accommodative force in the patient based on the relative motion and to determine at least one parameter for an intraocular lens based on the accommodative force; and
   an interface adapted to output the at least one parameter for the intraocular lens.

2. The system of claim 1, wherein the sensor comprises a light source and a photosensor.

3. The system of claim 2, wherein the photosensor detects Purkinje reflections from an anterior surface of the eye and from at least one surface of the lens.

4. The system of claim 1, wherein the sensor is an optical coherence tomography (OCT) sensor.

5. The system of claim 1, wherein the sensor is an ultrasound sensor.

6. The system of claim 1, wherein the at least one parameter is a haptic tension for the intraocular lens.

7. The system of claim 1, wherein the at least one parameter is a fill volume for the intraocular lens.

8. A method of determining a parameter for an intraocular lens, comprising:
   measuring motion of a lens of a patient relative to a globe of the patient's eye;
   determining an accommodative force in the patient based on the relative motion;
   determining at least one parameter for an intraocular lens based on the accommodative force; and
   outputting the at least one parameter for the intraocular lens.

9. The method of claim 8, wherein the motion of the lens is measured using a light source and a photosensor.

10. The method of claim 9, wherein the photosensor detects Purkinje reflections from an anterior surface of the eye and from at least one surface of the lens.

11. The method of claim 8, wherein the motion of the lens is measured using an optical coherence tomography (OCT) sensor.

12. The method of claim 8, wherein the motion of the lens is measured using an ultrasound sensor.

13. The method of claim 8, wherein the at least one parameter is a haptic tension for the intraocular lens.

14. The method of claim 8, wherein the at least one parameter is a fill volume for the intraocular lens.

* * * * *